United States Patent
Kelly et al.

(10) Patent No.: US 11,307,050 B2
(45) Date of Patent: Apr. 19, 2022

(54) MEASURING METHOD AND DEVICE

(71) Applicant: Koneksa Health Inc., New York, NY (US)

(72) Inventors: Peter John Kelly, London (GB); Robert David Ellis, London (GB); Chengrui Huang, New York, NY (US)

(73) Assignee: Koneksa Health Inc., New York, NY (US)

( * ) Notice: Subject to any disclaimer, the term of this patent is extended or adjusted under 35 U.S.C. 154(b) by 0 days.

(21) Appl. No.: 16/900,618

(22) Filed: Jun. 12, 2020

(65) Prior Publication Data
US 2021/0389159 A1  Dec. 16, 2021

(51) Int. Cl.
*G01C 22/00* (2006.01)
*G01P 15/18* (2013.01)

(52) U.S. Cl.
CPC ............ *G01C 22/006* (2013.01); *G01P 15/18* (2013.01)

(58) Field of Classification Search
CPC ............................... G01C 22/006; G01P 15/18
USPC .......................................................... 702/141
See application file for complete search history.

(56) References Cited

U.S. PATENT DOCUMENTS

| | | | |
|---|---|---|---|
| 10,330,491 B2 | 6/2019 | Janardhanan et al. | |
| 2003/0139692 A1 | 7/2003 | Barrey et al. | |
| 2006/0284979 A1 | 12/2006 | Clarkson | |
| 2012/0254934 A1 | 10/2012 | McBrearty et al. | |
| 2014/0156215 A1* | 6/2014 | Eastman | A61B 5/112 702/141 |
| 2014/0257535 A1 | 9/2014 | Morris et al. | |
| 2016/0217266 A1 | 7/2016 | Damani et al. | |
| 2017/0000384 A1 | 1/2017 | Annegarn et al. | |
| 2017/0095181 A1* | 4/2017 | Hauenstein | G01C 22/006 |
| 2018/0192917 A1* | 7/2018 | Piijl | G01C 25/005 |
| 2019/0104951 A1 | 4/2019 | Valys et al. | |
| 2019/0113364 A1* | 4/2019 | Khedr | G01C 21/165 |

(Continued)

FOREIGN PATENT DOCUMENTS

EP  3459453 A1  3/2019

OTHER PUBLICATIONS

International Search Report for PCT/GB2021/051468 (dated Oct. 6, 2021).

(Continued)

*Primary Examiner* — Ricky Go
(74) *Attorney, Agent, or Firm* — Merchant & Gould P.C.

(57) ABSTRACT

An apparatus and method determine movement information for a user that carries an accelerometer whilst moving. The apparatus receives acceleration data from the accelerometer defined relative to a frame of reference of the accelerometer. A transformation is determined and applied to the acceleration data or to data derived from the acceleration data to determine acceleration data is a user frame of reference that includes a user direction of travel and a side to side direction transverse to the user direction of travel. The acceleration data or data derived from the acceleration data is analyzed to determine a time period corresponding either to a user stride period or to a step period as the user is walking or running; and information about accelerations in the side to side direction are used to disambiguate whether the determined time period corresponds to the user stride period or to the user step period.

31 Claims, 9 Drawing Sheets

(56) References Cited

U.S. PATENT DOCUMENTS

2020/0202117 A1    6/2020  Wu et al.
2020/0333137 A1*  10/2020  Cutri ..................... G01P 15/08
2021/0169374 A1    6/2021  Vissiere et al.
2021/0389342 A1   12/2021  Kelly et al.

OTHER PUBLICATIONS

Karol Waga et al., "Detecting Movement Type by Route Segmentation and Classification", Colaborative computing: Networking, Applications and Worksharing (collaboratecom): 508-513 (2012).
Interational Search Report and Written Opinion for PCT/GB2021/051467 (dated Sep. 9, 2021).

* cited by examiner

MEASURING METHOD AND DEVICE

FIELD OF THE INVENTION

The present invention relates to the field of measurement of movement of a user. The invention has particular although not exclusive relevance to methods and devices for measuring and/or analysing the movement of a user to determine the step and stride periods of a user.

BACKGROUND

Devices such as activity monitors or pedometers are used to measure movements of a user. These devices can be used to determine when a user is walking and from this, the number of steps, or step count, of the user can also be determined.

Current devices are typically aimed at the leisure market—where accuracy is less important than repeatability. The devices may be dedicated devices designed to monitor the user's steps or they may take the form of a software application running on a user device such as a mobile (cellular) telephone or a smart watch or the like. As anyone who has used these devices will be aware, the different devices often give very different step counts even though the distance walked may be the same.

Existing methods and devices analyse the magnitude of the data generated by an accelerometer mounted in the user's device as the user is walking. Specifically, existing methods and devices typically either calculate the auto-correlation of this magnitude data over time periods or more crudely detect the spikes in the magnitude data corresponding to heel strikes, to work out periodic motions corresponding to the user's steps which are then counted. However, these analyses also capture other periodic motions such as the user's stride period (the period between a first heel striking the ground and the next time the first heel strikes the ground) which should be about twice the step period (the time interval between the first heel striking the ground and the second heel striking the ground). Typically, a user's step period when walking is less than about 0.8 seconds, and existing techniques typically compare the determined periods with this threshold in order to try to differentiate between step periods and stride periods. However, the inventors have realised that the existing methods, including this thresholding leads to errors in the calculations that are made.

A need exists for devices and methods that can determine more accurately the movements of the user. Such devices and methods can of course be used in the leisure market, where users will appreciate the more accurate information, but they can also help to open up new markets for this kind of analysis. For example, athletes are always looking for devices and methods that can accurately analyse their movements to allow them to improve their technique and gain an advantage over their competitors. Devices that are able to track and accurately monitor movements of the user can also be used in the medical field either for remote diagnosis purposes or for collecting data that may be relevant to a clinical study. For example, the movement information may be required for correlation with other sensors and time-specific measurements and the absence of this data may have a negative impact on determining the efficacy of therapies. For medical applications the requirement for accuracy is particularly important as it may affect treatment decisions and/or results of drug trials, which may have serious health consequences.

Some medical conditions, such as central nervous system disorders, may result in a subject having an atypical style of walking, so devices and algorithms optimised for the general (i.e. healthy) population may be inappropriate.

Some subjects may be unable or unwilling to wear a device in a specific position (e.g. ankle) or a specific device (e.g. a watch), so the device and algorithm should ideally be agnostic as regards to wear position and should be valid across a variety of hardware devices to accommodate these difficulties.

SUMMARY

Aspects of the invention are set out in the independent claims and preferred features are set out in the dependent claims.

According to a first aspect there is provided an apparatus and method for determining movement information for a user that carries an accelerometer whilst moving. The apparatus receives acceleration data from the accelerometer that are defined relative to a frame of reference of the accelerometer. A transformation is determined and applied to the acceleration data or to data derived from the acceleration data to determine acceleration data in a frame of reference of the user that includes a direction of travel of the user and a side to side direction transverse to the direction of travel of the user. The acceleration data or data derived from the acceleration data is analysed to determine a time period corresponding either to a stride period or to a step period of the user as the user is walking or running; and information about accelerations in the side to side direction are used to disambiguate whether the determined time period corresponds to the stride period of the user or to the step period of the user.

In some embodiments, the processor and memory are configured to use information about accelerations in said side to side direction and in said direction of travel to disambiguate whether the determined time period corresponds to the stride period of the user or to the step period of the user.

The processor and memory may determine a first autocorrelation function to determine said time period corresponding either to said stride period or to said step period of the user and may process the first autocorrelation function to identify a peak in the first autocorrelation function at an autocorrelation lag corresponding to the stride period of the user or to the step period of the user. In some embodiment, the processor and memory process the first autocorrelation function to identify the highest peak in the first autocorrelation function after a zero lag peak and determine the time period corresponding to the stride period of the user or to the step period of the user as the autocorrelation lag associated with the identified highest peak.

Typically, the processor and memory determine a second autocorrelation function of the accelerations in said side to side direction and disambiguate whether the time period corresponds to the stride period or the step period in dependence upon whether or not the second autocorrelation function includes a peak around the autocorrelation lag corresponding to the step or stride period.

A second autocorrelation function of the accelerations in said side to side direction and a third autocorrelation function of the accelerations in said direction of travel may be determined and used to disambiguate whether the time period corresponds to the stride period or the step period in dependence upon whether or not the second and autocorrelation function includes a peak around the autocorrelation lag corresponding to the step or stride period. The first, second and third autocorrelation functions may also be used to confirm that the user is walking or not walking.

The first autocorrelation function is calculated on said accelerometer data or on transformed accelerometer data that defines accelerations in the user frame of reference.

In one embodiment, the processor and memory are configured to determine and apply a first transformation that aligns a first axis of the accelerometer data or data derived from the accelerometer data with a vertical axis and a second transformation that aligns a second axis of the accelerometer data or data derived from the accelerometer data with said direction of travel and a third axis of the accelerometer data or data derived from the accelerometer data with said side to side direction. These transformations usually comprise a rotation.

In one embodiment, the processor and memory are configured to: determine that the determined time period corresponds to a stride period of the user when the information about accelerations in the side to side direction matches information about accelerations in the direction of travel; and determine that the determined time period corresponds to a step period of the user when the information about accelerations in the side to side direction does not match the information about accelerations in the direction of travel.

The frame of reference of the user usually comprises a vertical direction transverse to both the direction of travel and the side to side direction.

In one embodiment, the processor and memory are configured to process the acceleration data to identify periods of walking within the acceleration data and are configured to determine said time period corresponding either to a stride period or to a step period of the user using acceleration data from within an identified period of walking.

The direction of travel and the side to side direction may be identified as directions in a horizontal plane that have the most variability and the least variability in the received acceleration data. Alternatively, a compass or global positioning system (e.g. GPS) mounted in the user's device may provide direction of travel information.

The processor and memory may be configured to use the disambiguated step period or stride period to determine a step count of the user for movements corresponding to walking or running. This step count information may be stored and/or output to the user (e.g. on a display of the user device). The step count information may also be transmitted to a remote computer.

The invention also provides an apparatus for determining movement information for a user that carries an accelerometer whilst moving, the apparatus comprising one or more processors and memory configured to: receive acceleration data from the accelerometer, the acceleration data defining accelerations experienced by the accelerometer resulting from movement of the user, the accelerations being defined relative to a frame of reference associated with the accelerometer; apply to the acceleration data or to data derived from the acceleration data a transformation for transforming the frame of reference to a frame of reference of the user that includes a direction of travel of the user and a side to side direction transverse to the direction of travel of the user; determine a first autocorrelation function of the acceleration data or data derived from the acceleration data; determine a second autocorrelation function of accelerations in said direction of travel; determine a third autocorrelation function of accelerations in said side to side direction; and determine if the user is walking or not walking using the first, second and third autocorrelation functions.

The invention also provides an apparatus for determining movement information for a user that carries an accelerometer whilst moving, the apparatus comprising one or more processors and memory configured to: receive acceleration data from the accelerometer, the acceleration data including for each of a plurality of time points, acceleration values for a first plurality of orthogonal directions defined by an orientation of the accelerometer, each acceleration value representing acceleration of the accelerometer in one of the first plurality of orthogonal directions at a given time point; transform the acceleration data to transformed acceleration data that includes for each of the plurality of time points, acceleration values for a second plurality of orthogonal directions defined by an orientation of the user, each acceleration value representing acceleration movements of the accelerometer in one of the second plurality of orthogonal directions, the second plurality of orthogonal directions including a direction of travel of the user and a side to side direction transverse to the direction of travel of the user; analyse the acceleration data or at least part of the transformed acceleration data to determine a time period corresponding either to a stride period or a step period of the user; and use the transformed acceleration data relating to movements of the user in at least said side to side direction to disambiguate whether the determined period corresponds to the stride period of the user or to the step period of the user.

The apparatus summarised above may form part of a user device (such as a mobile (cellular) telephone, a smart watch or the like) carried by the user and the accelerometer may form part of the user device or may be in a separate device that communicates with the user device. The apparatus summarised above may also form part of a central server that receives acceleration data from the user device and that processes the received acceleration data to determine the movement information.

The invention also provides a method for determining movement information for a user that carries an accelerometer whilst moving, the method comprising: receiving acceleration data from the accelerometer, the acceleration data defining accelerations experienced by the accelerometer resulting from movement of the user, the accelerations being defined relative to a frame of reference associated with the accelerometer; applying to the acceleration data or to data derived from the acceleration data a transformation for transforming the frame of reference to a frame of reference of the user that includes a direction of travel of the user and a side to side direction transverse to the direction of travel of the user; analysing the acceleration data or data derived from the acceleration data to determine a time period corresponding either to a stride period or to a step period of the user as the user is walking or running; and using information about accelerations in said side to side direction to disambiguate whether the determined time period corresponds to the stride period of the user or to the step period of the user.

The invention also provides a computer program product (which may be a tangible computer readable medium or a carrier signal) comprising computer implementable instructions for causing a programmable computer device to become configured as the apparatus summarised above.

The invention also provides a clinical trial system and method comprising a central computer that communicates with a plurality of user devices, each user device being arranged to collect acceleration data relating to movement of the user associated with the user device; and wherein the central computer or at least one user device comprises an apparatus as summarised above.

BRIEF DESCRIPTION OF THE DRAWINGS

Exemplary embodiments of the invention will now be described with reference to the accompanying figures in which.

In the drawings, like reference numerals are used to indicate like elements.

DETAILED DESCRIPTION

Overview

As summarised above, the invention provides alternative ways for analysing a user's movements. The methods and devices provided by the invention can be used in various applications, such as in fitness trackers and the like. However, the invention can also be used in a medical setting which will now be described.

Figure 1A:
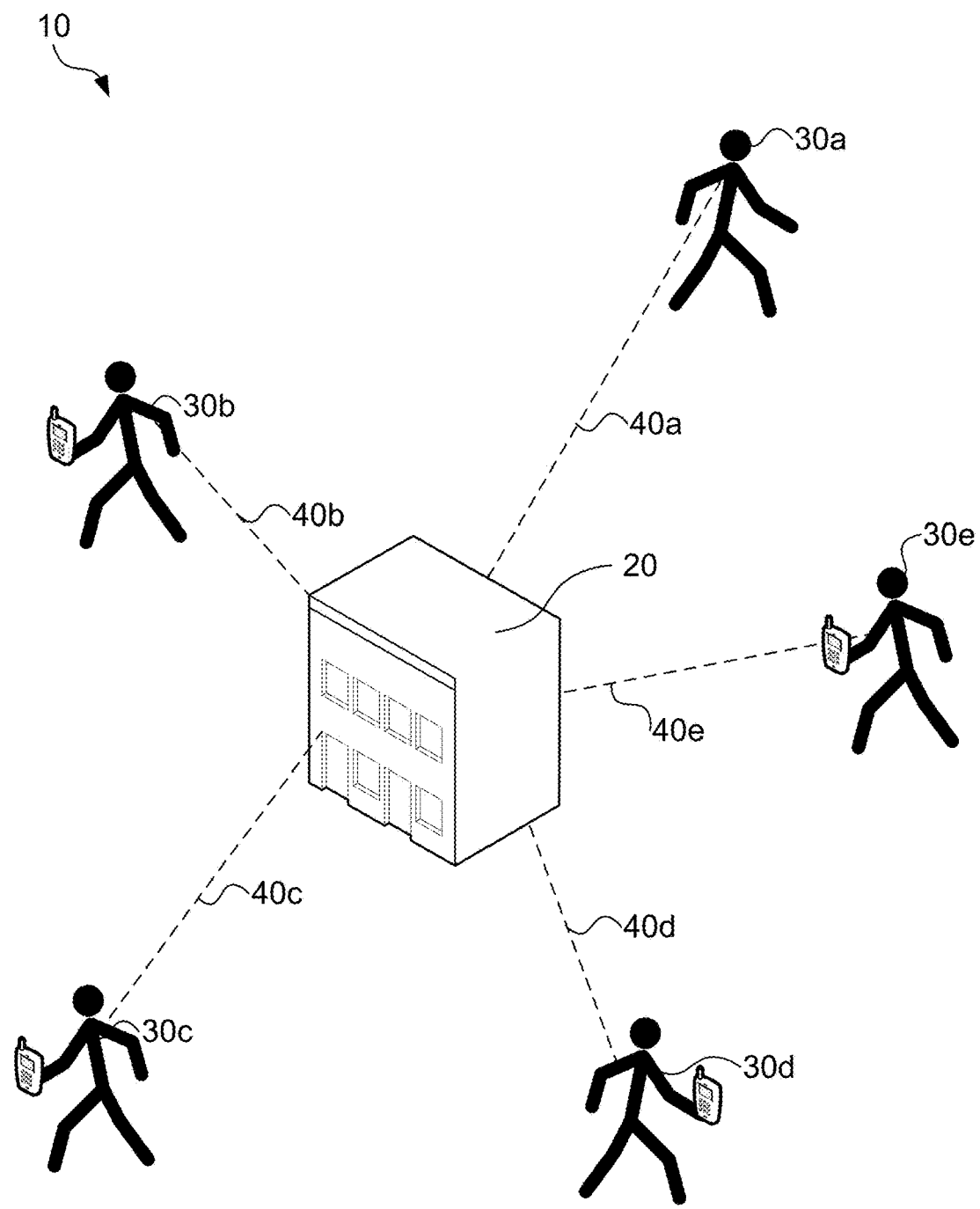
FIG. 1A schematically illustrates a clinical trial in which the movement of users taking part in the trial is determined by user devices worn or carried by the users and reported to a central server for collection and analysis.
Figure 1B:
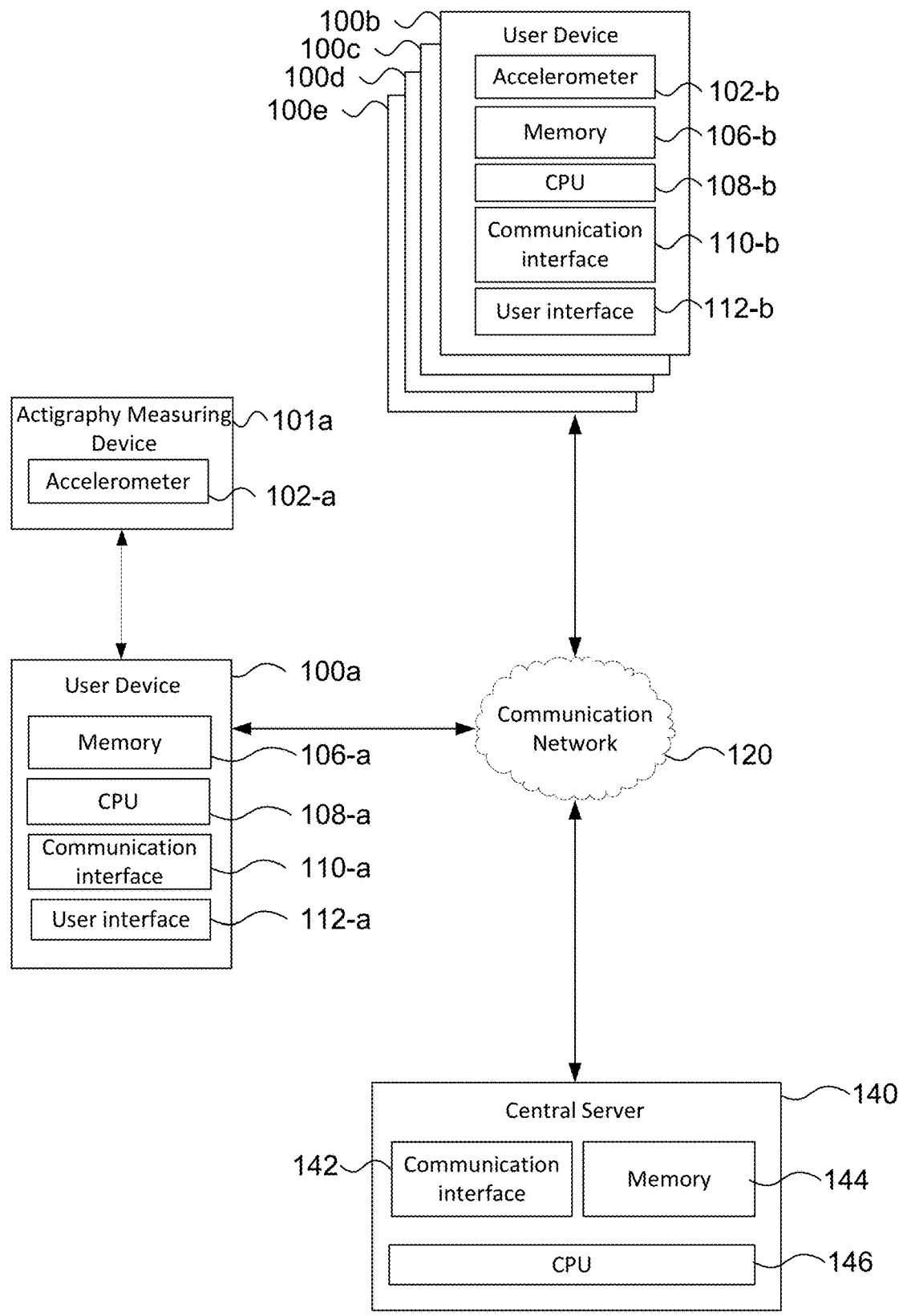
FIG. 1B is a block diagram illustrating the main electronic parts of the system shown in FIG. 1A.

More specifically, FIGS. 1A and 1B illustrate how the invention can be used in a clinical trial system 10 in which a number of subjects (also referred to below as users) 30a to 30e use a respective user device 100a to 100e to monitor the movements of the corresponding subject when they are walking. The information gathered by the user devices 100 is transmitted over a communication network 120 (represented in FIG. 1A by the broken lines 40a to 40e) back to a central server 140 with results that may be displayed within the clinic 20.

The clinic 20 may be a health centre such as a hospital or doctor's surgery. It may comprise a single centre or a number of centres located in a number of different geographical locations. The subjects 30 a-30e are patients of the clinic 20 and are taking part in a medical trial, organised by the clinic 20. Each of the patients in the medical trial are cohorted into groups with the same medical condition.

Each of the subjects 30 a-30e is provided with a user device 100 that may be dedicated to the clinic and returned to the clinic after the trial is over. Alternatively, the clinic may provide the subject with a software application that they can run on their own user device—such as a cellular telephone or a smart watch or the like. In either case, each subject is asked to wear or carry their user device so that an accelerometer associated with the user device can capture the movements of the user during the clinical trial. As shown in FIG. 1B, some user devices 100 have a built-in accelerometer 102 but some (in this example user device 100a) do not. Where the user device 100 does not have an accelerometer, a separate actigraphy measuring device 101 is provided that has an accelerometer 102-a for capturing the movements of the subject 30 a. The actigraphy measuring device 101 is worn or carried by the subject, for example, around the subject's wrist, ankle, in a pocket, on a belt, held in a hand, placed in a bag worn by the subject or worn as a pendant, for example around the subject's neck.

Accelerometers typically provide acceleration information in three orthogonal directions which depend on the orientation of the accelerometer. By analysing the accelerometer data, the user device 100 can determine movement information about the subject which is then transmitted (wirelessly or over a wired connection) as subject data to the central server 140 for further analysis as part of the medical trial.

In one example, the subject data provided to the central server 140 comprises walking data and identification data that identifies the subject to which the walking data relates. The walking data may comprise one or more of: step count, walking or activity periods, and distance walked, over a period specified by the trial, for example a day, week, month or year. The subject data may be retrieved from the user device 100 when the subject visits the clinic, or the subject data may be transmitted to the clinic over a cellular or wired telephone or computer network (wirelessly or over a wired connection). Subject data collected at the clinic can be supplemented with physical observations and tests which can only be done at the clinic 20 and not monitored remotely. Accuracy of the data provided to the clinic 20 about a subject's activity outside of the clinic 20 and at home is important in ensuring that the medical trial receives a true representation of the subject's activity during the monitored period. This can help to determine the efficacy of the clinical trial's therapies.

In another example, the subject data provided to the central server 140 comprises the identification data for the subject together with the accelerometer data, so that the central server 140 processes the accelerometer data for each subject from which the central server 140 works out the walking data for each subject itself. Although not illustrated in FIG. 1B, in this case, the central server 140 further comprises a user interface including a user input device such as a keyboard, and/or software for processing the data collected from the user devices of the system.

The subject data indicating activity of the subject, such as walking data, is a good indicator of health or fitness levels of the subject. For example, it can be used as an indicator of recovery because step count is an indicator of general health. An increase in step count shows increased mobility, which can indicate a patient's improvement, whilst a decrease or stagnation of step count could indicate that a patient is not responding to treatment or is not showing an improvement, or even that a patient is getting more ill. An increase in step count during time periods when the treatment's effects are greatest compared to when the effect of the treatment has worn off may give an indication of the efficacy of the treatment. In some cases, step count may be indicative of a need for a patient to be called into the clinic or could indicate that the patient may be required to spend a short amount of time in hospital. In some examples, the collected patient data may be used by the clinic to help book appointments for the patient with a doctor or clinician as required.

The walking data provided by the user devices can also be used to provide one or more of the plurality of subjects 30 a-30e with personalised exercise plans, tailored to their individual needs and or capabilities as indicated by the data. Prompts may be sent to a subject to encourage them to be active if their step count is too low.

Walking data is particularly useful to study in patients having one or more medical conditions which are known to affect walking capabilities. In some cases, temporary gait or balance complications may be caused by injury, trauma, inflammation or pain. In other cases, problems with walking such as gait, balance and coordination can be caused by specific conditions. Some of the conditions which may be particularly important in measuring walking activity include but are not limited to: arthritis, multiple sclerosis (MS), Meniere's disease, brain damage for example caused by a haemorrhage or tumour, Parkinson's disease, orthopaedic surgery on hips or lower body, cancer and associated therapies, cerebral palsy, obesity, gout, muscular dystrophy, stroke, spinal injury, deformities, etc.

The step and stride count data can also be used for athletic performance measurement and management. Detailed analysis of step and stride counts during targeted assessments of athletic activities can be provided to the athletes or their trainers and coaches. That data can then be used to inform training regimens to improve athletic performance.

The step and stride count data can also be used for physical therapy performance measurement and management. Detailed analysis of step and stride counts during targeted assessments during managed or unmanaged therapy sessions activities can be provided to the patient or their therapists and doctors. That data can then be used to inform therapeutic regimens to improve recovery programs.

User Device

Figure 2:
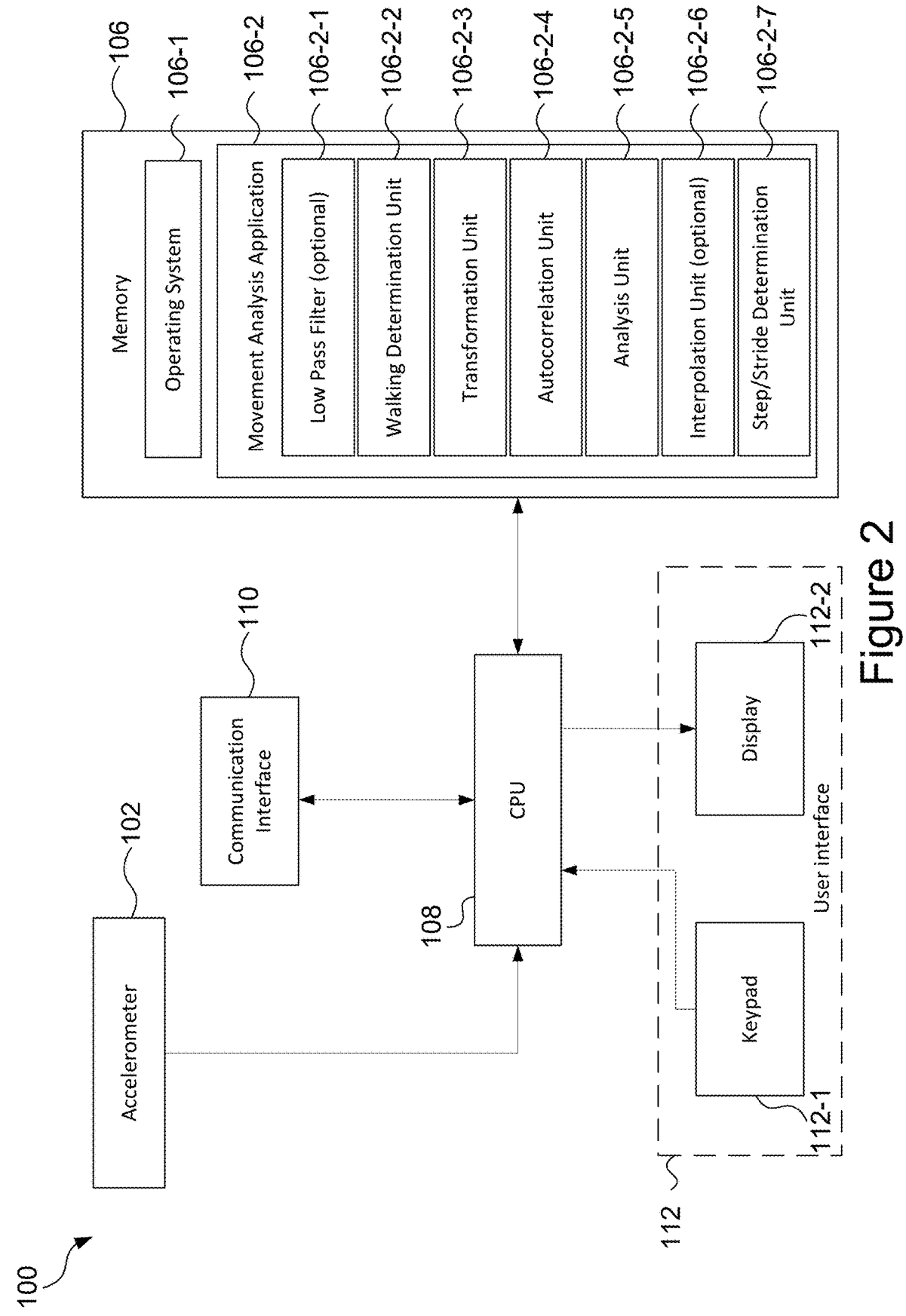
FIG. 2 is a block diagram illustrating the main components of a user device shown in FIG. 1B.

FIG. 2 is a block diagram of a typical user device 100 that is used in the system described above. As shown, in this case, the user device 100 has an accelerometer 102 that provides accelerometer data to at least one central processing unit (CPU) 108. The operation of the CPU 108 is controlled by software instructions that are stored in memory 106. As shown, the software instructions include an operating system 106-1 and a movement analysis application 106-2. The accelerometer data from the accelerometer 102 is processed by the movement analysis application 106-2 to work out the walking data for the subject.

The user device 100 also includes a communication interface 110 for communicating the subject data determined by the movement analysis application 106-2 to the central server 140; and a user interface 112 comprising a keypad 112-1 and a display 112-2 to allow the subject to interact with the user device 100. The display 112-2 may display one or more icons configured to provide information to the user and/or one or more of: time, date, number of steps, activity specific icons (walking running, cycling, etc.), activity duration, reminder messages and/or instructions concerning activity, network connection status, remaining battery power and any other useful information to be displayed to the user.

Accelerometer Data Analysis

Figure 3:
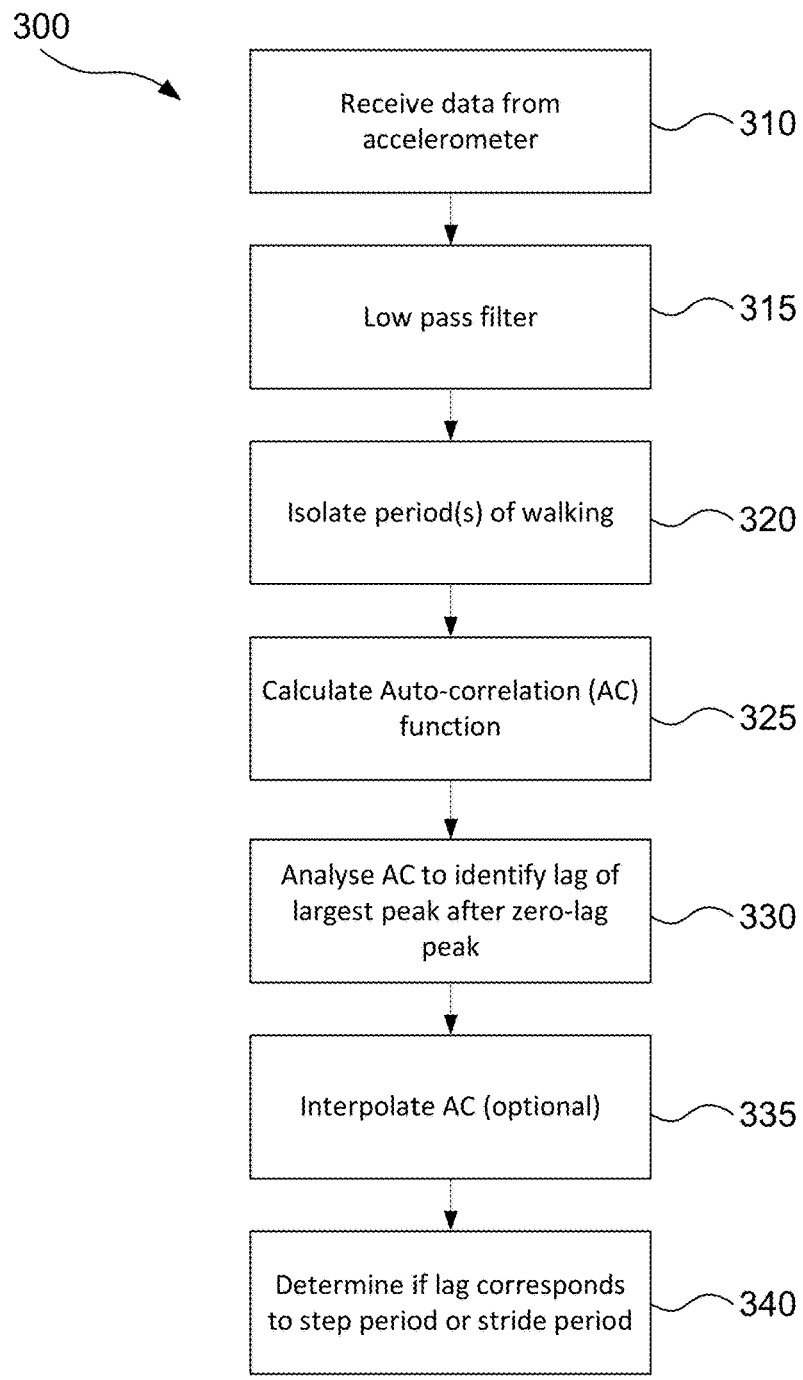
FIG. 3 is a flow diagram illustrating a prior art technique for determining the step or stride period of a user.

Before describing the way in which the movement analysis application 106-2 processes the accelerometer data, a description will be given with reference to FIG. 3 of the conventional way in which fitness trackers and the like process accelerometer data to determine steps taken by the user.

In step 310, data from the accelerometer 102 is received. The accelerometer data comprises a series of data points indexed by time, with the data point (reading) from the accelerometer at time t comprising acceleration measurements ($A_{Ax}(t)$, $A_{Ay}(t)$, $A_{Az}(t)$) in the three orthogonal directions: Ax, Ay and Az that are aligned with (defined by) the orientation of the accelerometer 102, rather than the orientation of the person carrying the accelerometer or any other geographic coordinate system. Readings from the accelerometer 102 are typically provided in units of g, where g is acceleration due to gravity at the Earth's surface (9.8 m/s$^2$). Sampling rates (the rate at which the accelerometer 102 provides the acceleration readings) will vary between accelerometers and are often configurable, but to be useful for analysing walking, the sampling rate should be at least 20 Hz, preferably higher (e.g. 30 Hz or 100 Hz).

Upon receiving the accelerometer data, conventional devices low pass filter the data to remove high frequency variations in the accelerometer data that are unrelated to walking movement of the user. The low pass filter will typically have a cut-off frequency of about 10 Hz. In step 320, the time series accelerometer data is processed to identify periods of walking from other periods in which the user is not walking. There are various methods by which this determination can be made. Typically, the conventional way to isolate periods of walking from other periods is to compare the magnitude of the accelerometer data with a threshold to identify periods of activity which may correspond to walking. The magnitude of the acceleration data provided at time t may be calculated as follows: $A_{mag}(t) = \text{sqrt}(A_{Ax}(t)^2 + A_{Ay}(t)^2 + A_{Az}(t)^2)$. Periods thus identified are then analysed to determine if their periodic patterns correspond to those of walking (i.e. are consistent with typical stride or step periods). In step 325, an autocorrelation analysis is performed to detect periodic patterns in the time series magnitude data calculated during step 320. Specifically, the autocorrelation unit 106-2-3 calculates the autocorrelation of the time series magnitude data M(t) obtained in each isolated period of walking (or section of walking) that is identified in step 320. That is the autocorrelation unit 106-2-3 calculates:

$$AC(k) = \Sigma_{n=1}^{T-k} A_{mag}(n) \cdot A_{mag}(n-k)$$

Where AC(k) is the autocorrelation at lag k; $A_{mag}(n)$ is the accelerometer magnitude at time n within the isolated period (section) of walking; and T is the number of magnitude values within the isolated period of walking. The autocorrelation function of each period of walking is calculated. Thus, if step 320 isolates twenty periods of walking, then in step 325, the autocorrelation unit 106-2-3 calculates twenty autocorrelation functions—one for each isolated period of walking.

Figure 4:
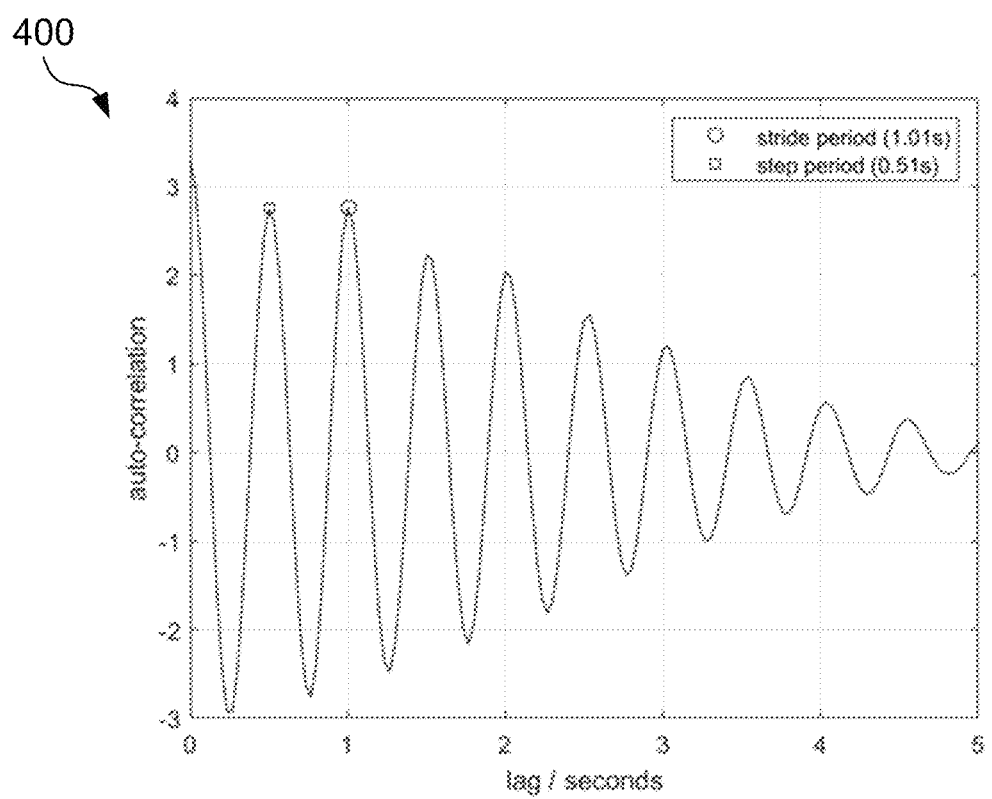
FIG. 4 is a plot illustrating an autocorrelation function calculated from the accelerometer data obtained whilst the user is walking.

In step 330, each autocorrelation function that is calculated in step 325 is analysed to determine the lag where the highest peak after the zero-lag peak is to be found in the autocorrelation function. The calculated lag corresponds to either the user's stride period or the user's step period. To illustrate this analysis, FIG. 4 is a plot representing the autocorrelation function that is determined in step 325 for one of the isolated periods (sections) of walking. The auto-correlation function is symmetric about zero-lag (k=0) and only the part corresponding to non-negative lags is shown in the plot. The peaks corresponding to the stride and step periods are marked with a circle and a square respectively. The typical stride period is between 1.0 and 1.2 seconds (100-120 steps per minute) and the typical step period will be half of this value.

The part of the autocorrelation function calculated between zero-lag and the first point at which the autocorrelation function is less than zero is considered to be the zero-lag peak. The lag of the highest peak in the autocorrelation function after the zero-lag peak is taken to be either the step or the stride period. As the autocorrelation function is calculated at a plurality of defined lags, the autocorrelation values that are calculated may not include the autocorrelation value exactly at the peak. A potentially more accurate estimate for the lag corresponding to the peak in the autocorrelation function can be determined using interpolation. This can be achieved, for example, by fitting a second-order polynomial to the calculated peak value and its neighbour on either side, and taking the peak of the polynomial function as the peak of the autocorrelation function to work out a more accurate value of the lag corresponding to the highest peak.

In step 340, a determination is made as to whether the lag corresponding to the identified highest peak corresponds to a step period or a stride period of the user. Depending on how symmetric the user's gait is and also the wear position of the accelerometer, the lag calculated in step 330 (or 335) may correspond to either the step or the stride period. For example, assuming the subject's gait is symmetric, if the accelerometer is worn/held centrally to the user's body, e.g. a phone held in front of the chest, or a device attached to the small of the user's back, then a left step and a right step will produce very similar magnitudes of acceleration at the accelerometer and the lag that is calculated is likely to correspond to the step period. On the other hand, if the accelerometer is attached to an ankle or wrist, then the left and right steps may result in substantially different acceleration data and the lag that is calculated is likely to correspond to the stride period.

In the example autocorrelation function illustrated in FIG. 4, the peak in the autocorrelation function at a lag of 0.5 seconds is almost as high as the peak in the autocorrelation function at a lag of 1.0 seconds and a slight variation in the accelerometer data might change which peak is the highest and therefore which peak is identified as the highest peak in step 330.

To determine whether the highest peak found in the autocorrelation function corresponds to the stride period or the step period, conventional fitness devices compare the determined lag with a threshold value. For a particular individual at a particular moment in time, the step period will be half the stride period (assuming the right step period and the left step period are identical). Therefore, if the lag that is found is below the threshold value (e.g. 0.8 seconds), then it can be assumed that the highest peak corresponds to the step period; and if the lag is found to be above the threshold, then it can be assumed that the highest peak corresponds to the stride period.

The determined step/stride period that is calculated for each of the isolated periods of walking is then used to calculate various characteristics of the user's walking—such as the number of steps taken, the length of time the user has walked etc. and this information is output (typically displayed) to the user and/or to a central server.

However, across a given population there will be an overlap between stride and step periods: the step period of some individuals might be longer than the stride period of others. Therefore, using thresholding to try to determine if a calculated lag period corresponds to a step period or a stride period is imperfect and will lead to errors. Calibration of the user device to the individual carrying the device or providing additional knowledge about the individual (e.g. their height) may help to reduce these errors. However, even for a particular individual there may be overlap between their stride and step periods, depending on their gait at any moment in time (e.g. running vs walking). Thus, in a material proportion of cases, using a threshold calculation to determine if a calculated lag period corresponds to a step period or a stride period will result in the wrong conclusion and this will affect the accuracy of the step counts that are obtained. For example if it is determined that the calculated lag period corresponds to the step period whilst in reality it corresponds to the stride period, then the number of steps calculated will be half the true value, which is likely to have knock-on effects on the estimations of other parameters, such as speed and distance travelled. Conversely if it is determined that the calculated lag period corresponds to the stride period whilst in reality it corresponds to the step period, then the number of steps calculated will be twice the true value.

Measurement Analysis Application

The measurement analysis application 106-2 has been developed to at least reduce some of these errors with conventional systems and to determine more accurate step and/or stride information from the accelerometer data. The way in which the measurement analysis application 106-2 operates in this embodiment will now be described in detail.

Figure 5A:
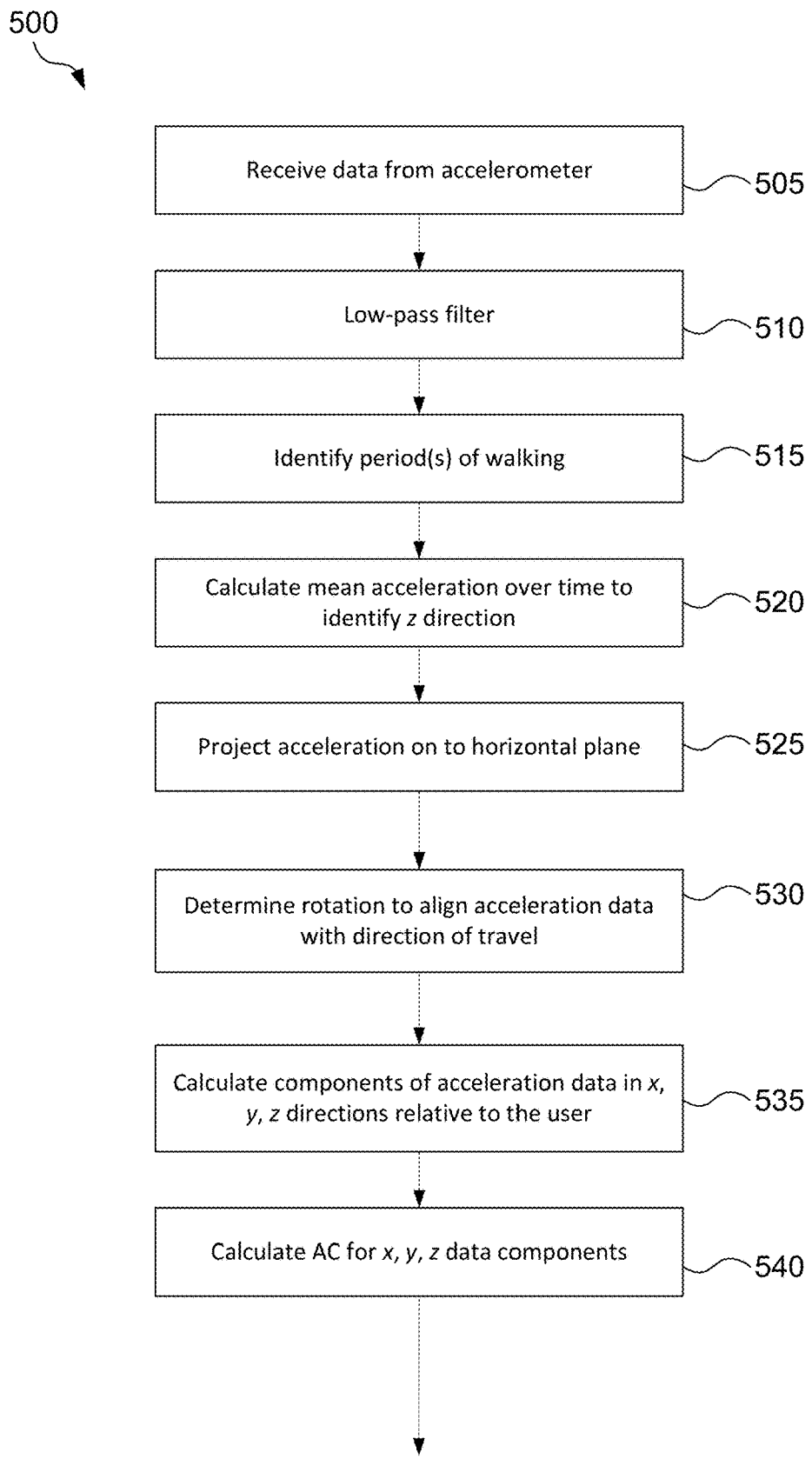
FIGS. 5A and 5B are a flow diagram illustrating a preferred technique for determining and disambiguating the step and stride period of a user whilst walking.
Figure 5B:
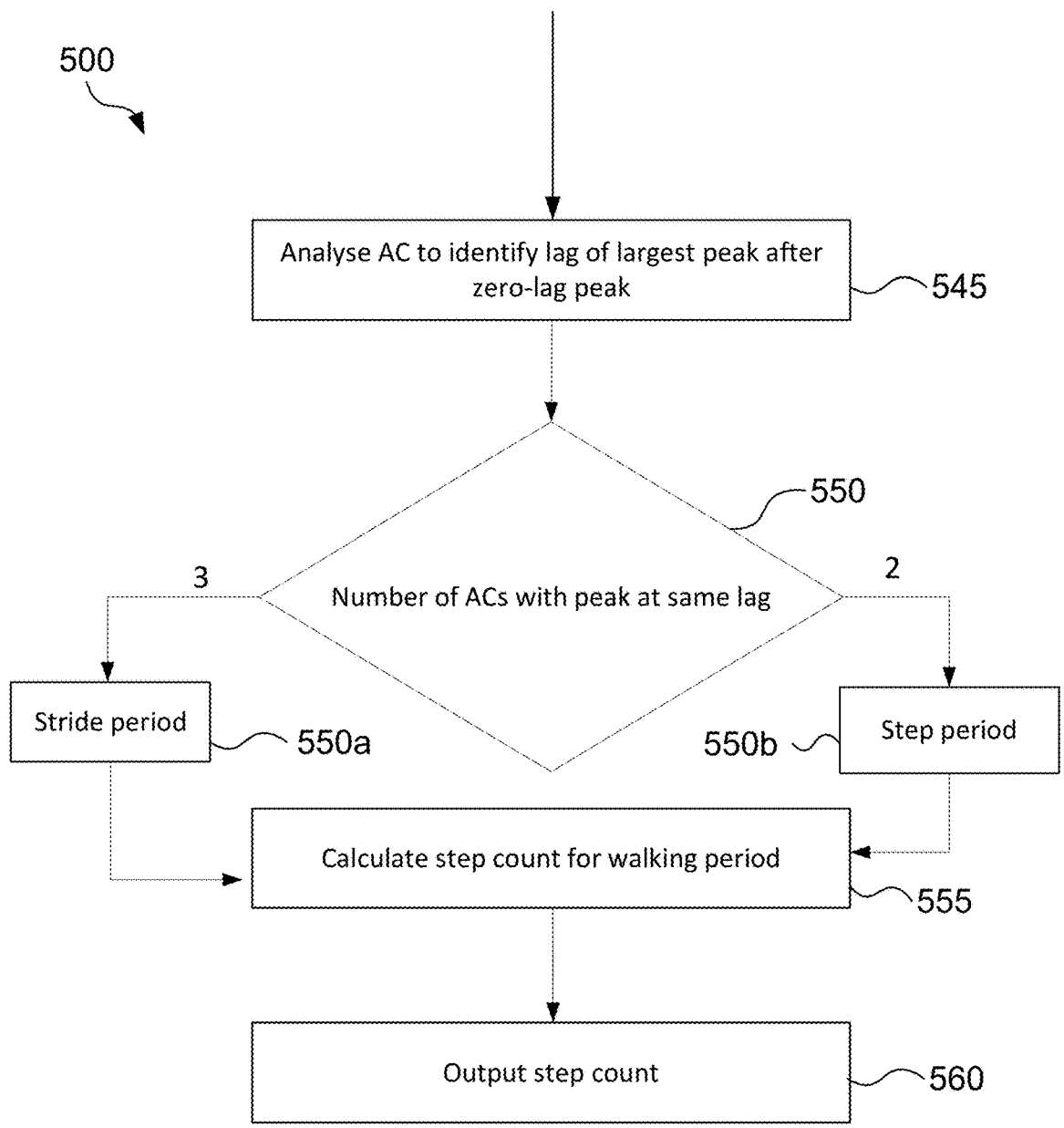

Referring to FIGS. 2 and 5, the measurement analysis application 106-2 receives, in step 505, the time series measurement data from the accelerometer 102. As discussed above, the acceleration data from the accelerometer at time t is defined as $(A_{Ax}(t), A_{Ay}(t), A_{Az}(t))$, with the accelerations being calculated along the three orthogonal directions: Ax, Ay and Az that are defined by the orientation of the accelerometer 102. Thus, each acceleration data point effectively defines a vector that defines the resulting direction of the acceleration experienced by the accelerometer 102 at the measurement time t. An optional low pass filter 106-2-1 filters the time series measurement data points received from the accelerometer in step 510, to remove high frequency variations in the accelerometer measurements that are not associated with walking movement of the user. The cut off frequency of the low pass filter is typically between 8 Hz and 20 Hz and preferably about 10 Hz.

In step 515, the walking period detection unit 106-2-2 processes the accelerometer data to detect periods when the user is walking or running. As discussed above, there are various ways that these periods can be detected. In a typical situation, an isolated period of walking will be about 10 to 20 seconds long. If longer time periods of walking are detected, these longer periods are usually split into sections, each of which is typically 10 to 20 seconds long.

A transformation unit 106-2-3 then processes the accelerometer data to project the measurements on to a co-ordinate reference frame defined by the orientation of the user walking—specifically so that z-axis is aligned vertically, the y-axis is aligned with the direction in which the user is travelling and the x-axis is aligned with the horizontal direction transverse to the direction of travel. In this embodiment, this is achieved in the following manner:

1) The mean acceleration vector over a period of time (several seconds) is determined in step 520:

$$A_{mean} = 1/N \sum_{n=1}^{N} A(n)$$

Where A(n) is the accelerometer data point at time n; N is defined by the sample rate of the accelerometer and the period of time over which the mean is computed. Gravity is the largest static component of acceleration measured by the accelerometer 102. The other accelerations experienced by the accelerometer will include accelerations in the forwards and backwards and side to side directions which to some extent cancel each other out when averaged over time. As a result, the mean vector calculated in step 520 identifies the vertical direction.

2) In step 525, the transformation unit 106-2-3 uses the determined mean vector to perform a first transformation that projects each acceleration data point from the accelerometer (A(t)—after low pass filtering if performed) onto the horizontal plane as follows:

$$A^{proj}(t)=A(t)-(A(t)\cdot A_{mean}{}^{U})A_{mean}{}^{U}$$

Where $A_{mean}{}^{U}$ is the unit vector of the mean acceleration vector determined in step 520. Whilst the z-axis of the resulting projected data points aligns with the vertical axis, the projected y-axis of the accelerometer is unlikely to align with the direction of travel (forwards and backwards direction) and the projected x-axis of the accelerometer is unlikely to align with the direction transverse to the direction of travel (side to side direction).

3) In step 530, the transformation unit 106-2-3 effectively works out the rotation needed to be applied to the projected acceleration data in order to align the projected x- and y-axes of the accelerometer with the desired side to side direction and forwards/backwards direction respectively. This rotation angle can be found in different ways. In this embodiment, the transformation unit 106-2-3 performs a principal component analysis (PCA) on the projected data (after setting the z-axis values in the projected data points to zero). The PCA analysis will identify the two orthogonal directions in the horizontal plane that have the most and the least variability. The direction with most variability will usually correspond to the movements in the forwards/backwards direction (y-direction) and the direction with least variability will usually correspond to the movements in the side to side direction (x-direction). The orthogonal directions identified by the PCA analysis effectively define the rotation within the horizontal plane that needs to be applied to the projected data points in order to align the projected x- and y-axes of the accelerometer with the desired side to side direction and forwards and backwards direction respectively.

4) In step 535, the transformation unit 106-2-3 applies the rotation determined in step 530 to the projected accelerometer data obtained in step 525. This generates, for the accelerometer data at time t, a transformed acceleration data point: $A_{rot}{}^{proj}(t)$ that identifies the acceleration in the vertical direction (the z-axis), the acceleration in the forwards-backwards direction (y-axis) and the acceleration in the side to side direction (x-axis).

In step 540, the autocorrelation unit 106-2-4 calculates the autocorrelation function of the vertical acceleration data (z-axis data), an autocorrelation of the forwards-backwards acceleration data (y-axis data) and an autocorrelation of the side to side acceleration data (x-axis data), for each of the isolated walking periods identified by the walking period determination unit 106-2-1. That is the following autocorrelations are calculated:

$$AC_z(k)=\Sigma_{n=1}^{T-k}Az_{rot}{}^{proj}(n)\cdot Az_{rot_{mag}}{}^{proj}(n-k)$$

$$AC_y(k)=\Sigma_{n=1}^{T-k}Ay_{rot}{}^{proj}(n)\cdot Ay_{rot_{mag}}{}^{proj}(n-k)$$

$$AC_x(k)=\Sigma_{n=1}^{T-k}Ax_{rot}{}^{proj}(n)\cdot Ax_{rot_{mag}}{}^{proj}(n-k)$$

where $Az_{rot}{}^{proj}(n)$ is the acceleration data in the vertical direction at time point n; $Ay_{rot}{}^{proj}(n)$ is the acceleration data in the forwards-backwards direction at time point n; $Ax_{rot}{}^{proj}(n)$ is the acceleration data in the side to side direction at time point n; k is the autocorrelation lag; and T is the number of acceleration data points within the isolated walking period.

It should be noted that the processing above may result in the x and y data being switched over—that is the y-axis data may actually correspond to the side to side acceleration measurements and the x-axis data may correspond to the forwards/backwards acceleration measurements. However, this does not matter—as will become evident from the following discussion.

Figure 6:
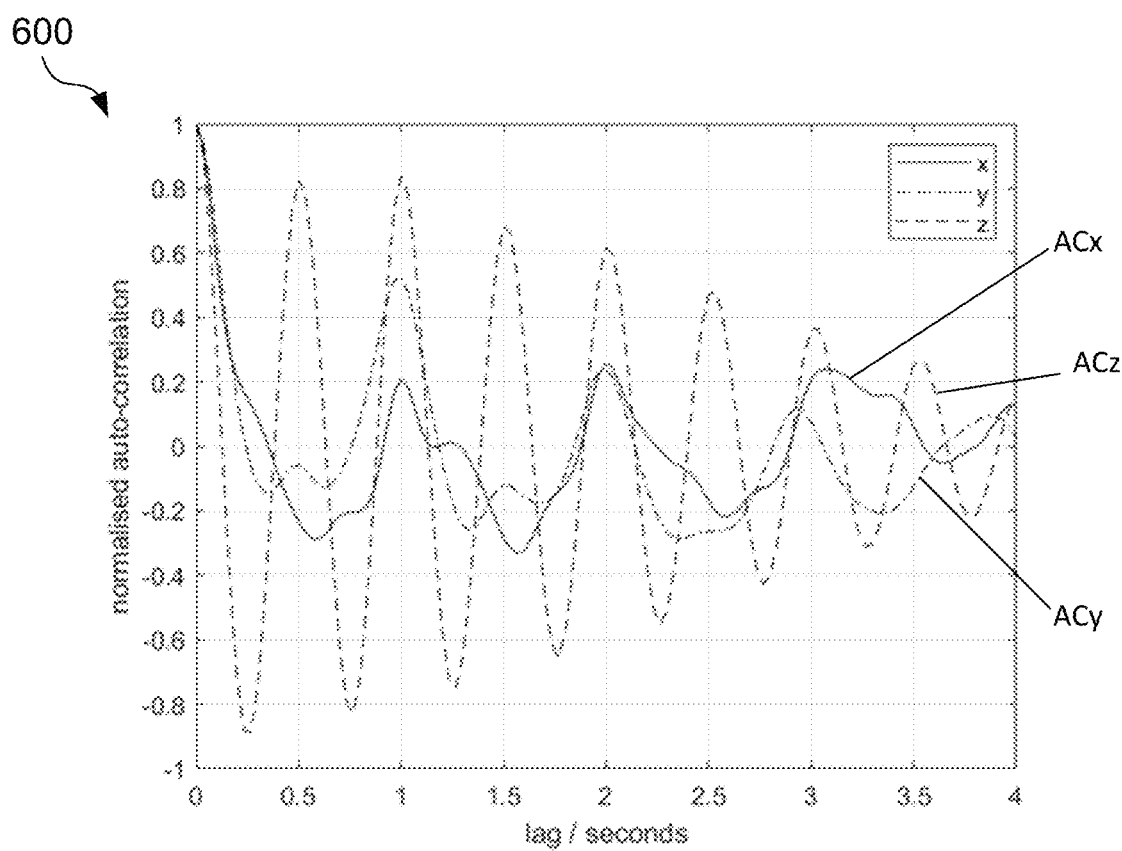
FIG. 6 is a plot illustrating autocorrelations calculated from the accelerometer data obtained whilst the user is walking and used to disambiguate step and stride periods.

FIG. 6 illustrates a plot of the three autocorrelation functions that are calculated for one of the isolated walking periods for lags (k) between 0 and 4 seconds. The autocorrelation function in the z (vertical) direction ($AC_z$) is generally much larger than the autocorrelation function in the x (side to side) direction ($AC_x$) and the autocorrelation function in the y (forwards/backwards) direction ($AC_y$), so each autocorrelation function shown in FIG. 6 has been scaled to be unity at zero lag for ease of comparison.

As can be seen from FIG. 6, the autocorrelation function for the z direction ($AC_z$), has a similar plot to the autocorrelation of the magnitude of the original acceleration data (as shown in FIG. 4) and has strong peaks at both 0.5 seconds (the step period) and at 1.0 seconds (the stride period). Again, however, the highest peak in $AC_z$ after the zero-lag peak may correspond to the step period or to the stride period. The autocorrelation function for both the x and y directions ($AC_x$ and $AC_y$) also have noticeable peaks at 1.0 second (the stride period). The data used to generate the example autocorrelation functions shown in FIG. 6 were obtained from a wrist-worn user device and the peak in the autocorrelation function $AC_y$ at the step period is present, but subdued. For centrally worn devices, the peak in the autocorrelation function $AC_y$ at the step period would be more pronounced. However, the autocorrelation function $AC_x$ lacks a peak at 0.5 seconds (the step period) regardless of how the user device is carried or worn.

Table 1 below summarises whether there is likely to be a peak in the autocorrelation functions for the vertical ($AC_z$), forwards-backwards ($AC_y$) and side-to-side ($AC_x$) directions at lags corresponding to the stride and step periods for different wear positions of the user device/accelerometer.

| | | Direction | | |
|---|---|---|---|---|
| Wear position | AC lag | Vertical $Ac_z$ | Forwards-backwards $Ac_y$ | Side-to-side $Ac_x$ |
| ankle/wrist | stride period | yes | yes | yes |
| ankle/wrist | step period | yes | maybe | no |
| central | stride period | yes | yes | yes |
| central | step period | yes | yes | no |

$AC_x$ is likely to exhibit a trough at the step period. The lack of a peak in $AC_x$ at the step period can be used to distinguish between whether the highest peak in $AC_z$ after the zero-lag peak corresponds to the stride period or the step period—without having to use thresholds.

Specifically, in step 545, the analysis unit 106-2-5 processes the autocorrelation values $AC_z$ obtained for the vertical direction to identify the lag corresponding to the largest peak after the zero-lag peak. As before, the optional interpolation unit 106-2-6 may use interpolation using a polynomial function to determine a more accurate estimate of the lag corresponding to this largest peak. Then, in step 550, the step/stride determination unit 106-2-7 determines if the autocorrelation functions for the x and y directions ($AC_z$ and $AC_y$) also have peaks at the lag identified in step 545. If both $AC_x$ and $AC_y$ also have peaks at (or around) this lag, then the step/stride determination unit 106-2-7 determines that the lag identified in step 545 corresponds to the stride period of the user. However, if only one (or neither) of $AC_x$ and $AC_y$ have a peak at the identified lag, then the step/stride determination unit 106-2-7 determines that the lag identified at step 545 corresponds to the user's step period. There are various different ways for determining if $AC_x$ or $AC_y$ exhibit a "peak": often there will be a peak (i.e. a sample of the auto-correlation that is higher than its neighbours on either side) at or near the lag identified in step 545. In other embodiments, if $AC_x$ or $AC_y$ at the determined lag is above a threshold, which may be zero or may be relative to the autocorrelation at zero lag, it is deemed to be a peak. It should be noted that this approach does not rely on the assumption that y corresponds to the forwards-backwards direction and x corresponds to the side-to-side direction; this approach is still valid if x corresponds to the forwards-backwards direction and y corresponds to the side-to-side direction.

Once the step/stride determination unit 106-2-7 has determined if the lag identified at step 545 corresponds to the user's step period or the user's stride period, the movement analysis application 106-2 can calculate in step 555 the number of steps taken by the user during the walking period. This information is then output in step 560. The step count may be output to the user on the display 112-2 and/or it may be transmitted together with other related walking data and an identifier to identify the user to whom the data relates to the central server 140 for use in the clinical trial.

Modifications and Variations

A detailed embodiment has been described above. Various modifications and changes can be made to the above embodiment. Some of these variations will now be described.

In the embodiment described above, there is an implicit assumption that the orientation of the accelerometer 102 remains the same (constant) within each of the isolated periods of walking determined in step 515 and over which the autocorrelation functions are calculated. It also assumes that the characteristics of the walking (in particular the step/stride periods) are relatively constant over the isolated period of walking. These assumptions may not be correct, especially for longer isolated periods of walking. To address this issue, the isolated walking periods may be divided into smaller subsections or epochs (that may or may not overlap in time) with the above analysis from step 520 then being performed on each smaller subsection of accelerometer data. The duration of each subsection should be at least 3 seconds long in order to encompass a number of strides. When the rotation is calculated in step 530 for a subsection, the PCA analysis may cause the determined rotation to change abruptly from one subsection to the next. Interpolation may be used (e.g. using the quaternion representation or other means) to provide a smooth transition between the rotations of adjacent subsections. Data from other sensors (in particular gyroscopes that may also be mounted in the user device) may also be useful to determine changes in orientation of the user device—and hence the changes in rotation required to align the acceleration data with the direction of travel of the user.

In the above embodiment, measurements from an accelerometer were resolved into a vertical direction (z) and into x and y directions corresponding to the user's direction of travel and side to side direction. Autocorrelation functions were then calculated for the measurements in the x, y and z directions. In an alternative embodiment, instead of determining the autocorrelation function of the acceleration data in the z-direction, the autocorrelation may be performed on the magnitude of the accelerometer data (either before or after transformation). The autocorrelation functions in the x and y directions would still be calculated and used as before in order to resolve the ambiguity over whether the highest peak after the zero-lag peak in the autocorrelation function of the magnitude data corresponds to the user's stride period or the user's step period.

In the above embodiment, the analysis unit 106-2-5 used a principal component analysis to work out the rotation needed to align the projected x and y axis of the accelerometer onto the walking direction and side to side direction of the user. Instead of using PCA to determine this rotation, a satellite navigation system (such as a GPS system) provided in the user device may provide the geographical direction that the user is walking in and a compass in the user device may provide the orientation of the device relative to the geographic axes and from this the analysis unit 106-2-5 can work out the rotation needed to map the acceleration data from the accelerometer onto the reference frame of the user walking (with y corresponding to the direction that the user is walking in, with x being transverse to y in the horizontal plane and with z being the vertical direction).

Alternatively if the device is at a fixed, known orientation to the user's direction of travel—for example if the device is held pointing in the direction of travel—then the rotation needed to map the acceleration data from the accelerometer onto the reference frame of the user may already be known.

The x, y, z autocorrelation functions calculated in the above embodiment may also be useful for distinguishing between walking and other activities. For example, walking detection algorithms can be tricked by a user with a wrist-worn user device swinging their arm—if the swing period is similar to a typical stride period, then the arm-swinging may be wrongly interpreted as walking. The autocorrelation data determined in the x, y, z directions can be used to confirm that a period of walking is actually a period of walking rather than the user moving the device to try to mimic walking movements.

Figure 7:
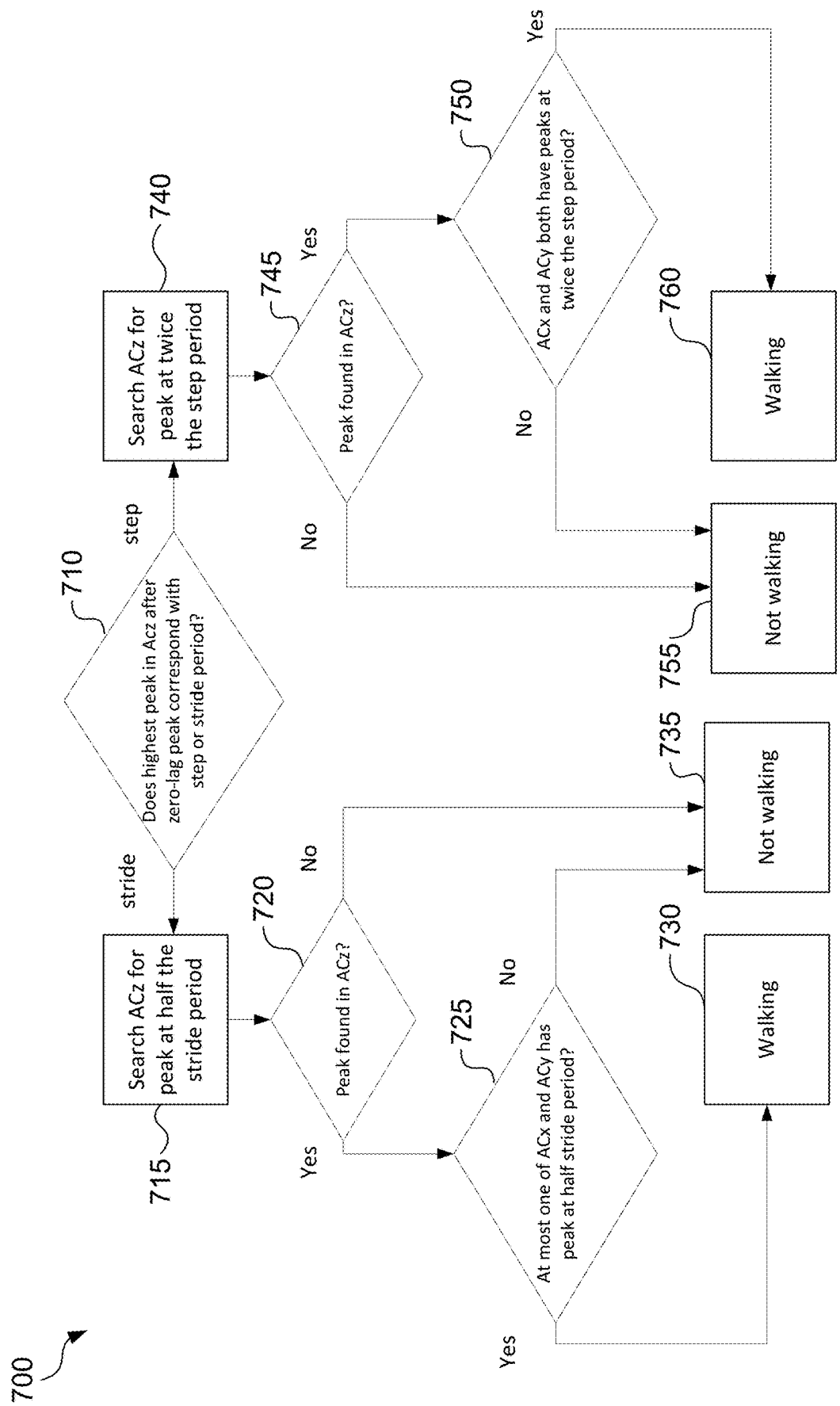
FIG. 7 illustrates a flow diagram illustrating a preferred way for determining whether a period of movement corresponds to a period of walking or not walking.

FIG. 7 is a flow diagram illustrating the way in which the system can determine more accurately whether a period of movement corresponds to a period of walking or to some other user movement that is trying to mimic walking.

In step 710, the device determines if the highest peak after the zero-lag peak in $AC_z$ (or in the autocorrelation of the magnitude accelerometer data) corresponds to the user's stride or step period (this effectively corresponds to the determination made at step 550 or 555 in FIG. 5). If the highest peak corresponds to the user's stride period, the process proceeds to step 715 and if the highest peak corresponds to a step period, the process proceeds to step 740.

At step 715 the walking determination unit 106-2-2 processes the autocorrelation function for the z (vertical) direction ($AC_z$) to determine if it has a peak at a lag that is half the lag corresponding to the stride period. At step 720 if a peak is found in $AC_z$ at half the stride period, the process proceeds to step 725. If a peak is not found in $AC_z$ at half the stride period, then the walking determination unit 106-2-2 determines at step 735 that the user is not actually walking in this period.

At step 725, the walking determination unit 106-2-2 checks the autocorrelation functions for the x and y directions ($AC_x$ and $AC_y$) to determine if at most one of $AC_x$ and $AC_y$ also contains a peak at half the stride period. If they both contain a peak at half the stride period, then the processing proceeds to step 735 where the walking determination unit 106-2-2 determines again that the movement in the current period is not actually walking. If neither or only one of $AC_x$ and $AC_y$ has a peak at half the stride period, then the processing moves to step 730 where the walking determination unit 106-2-2 confirms that the user is actually walking in the current period.

If the highest peak after the zero-lag peak in $AC_z$ corresponds to the user's step period, then in step 740 the walking determination unit 106-2-2 processes the autocorrelation function for the z (vertical) direction ($AC_z$) to determine if it has a peak at twice the step period. If a peak is not found in $AC_z$ at twice the step period, then the walking determination unit 106-2-2 determines at step 755 that the user is not actually walking in this period.

At step 750, the walking determination unit 106-2-2 checks the autocorrelation functions for the x and y directions ($AC_x$ and $AC_y$) to determine if both of them also contain a peak at twice the step period. If they do not both contain a peak at twice the step period, then the processing proceeds to step 755 where the walking determination unit 106-2-2 determines again that the movement in the current period is not actually walking. If both of $AC_x$ and $AC_y$ have a peak at twice the step period, then the processing moves to step 760 where the walking determination unit 106-2-2 confirms that the user is walking in the current period.

In the above embodiment, the step/stride determination unit considered the presence and absence of peaks in the forwards/backwards direction (y direction) and in the side to side direction (x direction), to disambiguate whether the lag period of the highest peak after the zero-lag peak corresponds to the step period or the stride period. The preferred technique counted peaks in the different autocorrelation functions at the same lag. This helps to avoid any errors where the forwards/backwards direction is mixed up with the side to side direction. In other embodiments, the device analysing the accelerometer data may simply assume that the determined side to side direction (x direction) is correct, and then may disambiguate whether the identified lag corresponds to the step period or the stride period in dependence upon whether the autocorrelation function for the x direction includes a peak at the identified lag. If it does, then it is the stride period and if it does not then it is the step period.

In the above embodiments, the accelerometer data obtained from the accelerometer was analysed by looking at the autocorrelation function of the data in the different directions. The autocorrelation analysis is good at highlighting periodic changes in the acceleration data—caused by repetitive movements such as walking and running. Other kinds of analysis could be performed to identify these periodic changes (and the period thereof). For example, a Fourier Transform (or other frequency analysis such as a Discrete Cosine Transform) could be determined and analysed to identify peaks in the frequency domain representative of the step or stride period.

Similarly, in the above embodiment, the acceleration data from the accelerometer is transformed from the co-ordinate reference frame of the accelerometer to the co-ordinate reference frame of the user and then the autocorrelation was performed on the transformed acceleration data. In an alternative embodiment, this transformation of the co-ordinate system may happen after the autocorrelation functions have been calculated. Thus, the original accelerometer data defining the accelerations of the accelerometer in directions Ax, Ay and Az may be subject to an autocorrelation analysis first and then the autocorrelations are transformed to account for the change in reference frame.

Further, in the case that the user's device has multiple accelerometers built into it, the data from each accelerometer may be analysed and the results combined (for example averaged) to work out more accurate or less noisy step and/or stride periods. Similarly, where the user is carrying multiple devices (such as a cellular telephone) and an actigraph device, where both devices have an accelerometer, the system can determine step and/or stride periods using the data from both accelerometers. The measurements from the two (or more) accelerometers can then be averaged again to improve signal to noise ratio or the measurements from one accelerometer may be used to corroborate or validate the step and/or stride period determined from acceleration data obtained from the other accelerometer.

In the above embodiment, a software application for processing accelerometer data was provided in the user device. The same or similar software may be provided in the computer of the central server—so that the central server performs the above step/stride analysis. This software application may be provided as computer implementable instructions on a carrier signal or on a tangible computer readable medium. Alternatively, the functions of the software application may be defined in hardware circuits such as in FPGA or ASIC devices.

It will be appreciated from the above description that many features of the different examples are interchangeable and combinable. The disclosure extends to further examples comprising features from different examples combined together in ways not specifically mentioned. Indeed, there are many features presented in the above examples and it will be apparent to the skilled person that these may be advantageously combined with one another.

The application also includes the following numbered clauses that define various aspects of the invention:

1. An apparatus for determining movement information for a user that carries an accelerometer whilst moving, the apparatus comprising one or more processors and memory configured to:
   receive acceleration data from the accelerometer, the acceleration data defining accelerations experienced by the accelerometer resulting from movement of the user, the accelerations being defined relative to a frame of reference associated with the accelerometer;
   apply to the acceleration data or to data derived from the acceleration data a transformation for transforming the frame of reference to a frame of reference of the user that includes a direction of travel of the user and a side to side direction transverse to the direction of travel of the user;
   analyse the acceleration data or data derived from the acceleration data to determine a time period corresponding either to a stride period or to a step period of the user; and
   use information about accelerations in said side to side direction to disambiguate whether the determined time period corresponds to the stride period of the user or to the step period of the user.

2. The apparatus according to clause 1, wherein the processor and memory are configured to use information about accelerations in said side to side direction and in said direction of travel to disambiguate whether the determined time period corresponds to the stride period of the user or to the step period of the user.

3. The apparatus according to clause 1 or 2, wherein the processor and memory are configured to determine a first autocorrelation function to determine said time period corresponding either to said stride period or to said step period of the user.
4. The apparatus of clause 3, wherein the processor and memory are configured to process the first autocorrelation function to identify a peak in the first autocorrelation function at an autocorrelation lag corresponding to the stride period of the user or to the step period of the user.
5. The apparatus of clause 4, wherein the processor and memory are configured to process the first autocorrelation function to identify the highest peak in the first autocorrelation function after a zero lag peak and to determine the time period corresponding to the stride period of the user or to the step period of the user as the autocorrelation lag associated with the identified highest peak.
6. The apparatus according to clause 4 or 5, wherein said processor and memory are configured to determine a second autocorrelation function of the accelerations in said side to side direction and are configured to disambiguate whether the time period corresponds to the stride period or the step period in dependence upon whether or not the second autocorrelation function includes a peak around the autocorrelation lag corresponding to the step or stride period.
7. The apparatus according to clause 4, 5 or 6, wherein said processor and memory are configured to determine a second autocorrelation function of the accelerations in said side to side direction and a third autocorrelation function of the accelerations in said direction of travel and are configured to disambiguate whether the time period corresponds to the stride period or the step period in dependence upon whether or not the second and autocorrelation function includes a peak around the autocorrelation lag corresponding to the step or stride period.
8. The apparatus according to clause 7, wherein the processor and memory are configured to use the first, second and third autocorrelation functions to confirm that the user is walking or running or not walking or not running.
9. The apparatus according to any of clauses 3 to 8, wherein said first autocorrelation function is calculated on said accelerometer data or on data derived from said accelerometer data.
10. The apparatus according to any of clauses 3 to 9, wherein said first autocorrelation function is calculated on transformed accelerometer data that defines accelerations in the user frame of reference.
11. The apparatus of any preceding clause, wherein the processor and memory are configured to determine and apply a first transformation that aligns a first axis of the accelerometer data or data derived from the accelerometer data with a vertical axis.
12. The apparatus of clause 11, wherein the processor and memory are configured to determine and apply a second transformation that aligns a second axis of the accelerometer data or data derived from the accelerometer data with said direction of travel and a third axis of the accelerometer data or data derived from the accelerometer data with said side to side direction.
13. The apparatus according to clause 12, wherein said second transformation comprises a rotation.
14. The apparatus according to any preceding clause, wherein the processor and memory are configured to:
determine that the determined time period corresponds to a stride period of the user when the information about accelerations in the side to side direction matches information about accelerations in the direction of travel; and
determine that the determined time period corresponds to a step period of the user when the information about accelerations in the side to side direction does not match the information about accelerations in the direction of travel.
15. The apparatus of any preceding clause, wherein the frame of reference of the user comprises a vertical direction transverse to both the direction of travel and the side to side direction.
16. The apparatus according to any preceding clause wherein the processor and memory are configured to process the acceleration data to identify periods of walking or running within the acceleration data and is configured to determine said time period corresponding either to a stride period or to a step period of the user using acceleration data from within an identified period of walking or running.
17. The apparatus according to any preceding clause wherein the direction of travel and the side to side direction are identified as directions in a horizontal plane that have the most and the least variability in the received acceleration data.
18. The apparatus according to any preceding clause, wherein the processor and memory are further configured to use the disambiguated step period or stride period to determine a step count of the user for movements corresponding to walking or running.
19. An apparatus for determining movement information for a user that carries an accelerometer whilst moving, the apparatus comprising one or more processors and memory configured to:
receive acceleration data from the accelerometer, the acceleration data defining accelerations experienced by the accelerometer resulting from movement of the user, the accelerations being defined relative to a frame of reference associated with the accelerometer;
apply to the acceleration data or to data derived from the acceleration data a transformation for transforming the frame of reference to a frame of reference of the user that includes a direction of travel of the user and a side to side direction transverse to the direction of travel of the user;
determine a first autocorrelation function of the acceleration data or data derived from the acceleration data;
determine a second autocorrelation function of accelerations in said direction of travel; determine a third autocorrelation function of accelerations in said side to side direction; and
determine if the user is walking or not walking or running or not running using the first, second and third autocorrelation functions.
20. An apparatus for determining movement information for a user that carries an accelerometer whilst moving, the apparatus comprising one or more processors and memory configured to:
receive acceleration data from the accelerometer, the acceleration data including for each of a plurality of time points, acceleration values for a first plurality of orthogonal directions defined by an orientation of the accelerometer, each acceleration value representing acceleration of the accelerometer in one of the first plurality of orthogonal directions at a given time point;
transform the acceleration data to transformed acceleration data that includes for each of the plurality of time points, acceleration values for a second plurality of orthogonal directions defined by an orientation of the user, each acceleration value representing acceleration movements of the accelerometer in one of the second plurality of orthogonal directions, the second plurality of orthogonal directions including a direction of travel of the user and a side to side direction transverse to the direction of travel of the user;

analyse the acceleration data or at least part of the transformed acceleration data to determine a time period corresponding either to a stride period or a step period of the user; and use the transformed acceleration data relating to movements of the user in at least said side to side direction to disambiguate whether the determined period corresponds to the stride period of the user or to the step period of the user.

21. An apparatus according to any preceding clause, wherein the apparatus forms part of a user device carried by the user and wherein the accelerometer forms part of the user device or is configured to communicate with the user device.

22. An apparatus according to any preceding clause, wherein the at least one processor and memory are configured to obtain acceleration data from a plurality of accelerometers carried by the user when walking or running and the step or stride period is determined using the acceleration data from the plurality of accelerometers.

23. An apparatus according to clause 22, wherein the at least one processor and memory are configured to determine a respective step or stride period using the acceleration data from each accelerometer and are configured: i) to average the step or stride periods obtained; or ii) to validate the step or stride period determined from the acceleration data from one accelerometer using the acceleration data or data derived from the acceleration data obtained from another accelerometer.

24. An apparatus according to clause 22 or 23, wherein the accelerometers are mounted in the same user device carried by the user or wherein the accelerometers are mounted in different user devices carried by the user.

25. An apparatus according to clause 24, wherein the accelerometers are mounted in different user devices carried by the user in different wear positions.

26. An apparatus for determining movement information for a user that carries an accelerometer whilst moving, the apparatus comprising:

means for receiving acceleration data from the accelerometer, the acceleration data defining accelerations experienced by the accelerometer resulting from movement of the user, the accelerations being defined relative to a frame of reference associated with the accelerometer;

means for applying to the acceleration data or to data derived from the acceleration data, a transformation for transforming the frame of reference to a frame of reference of the user that includes a direction of travel of the user and a side to side direction transverse to the direction of travel of the user;

means for analysing the acceleration data or data derived from the acceleration data to determine a time period corresponding either to a stride period or to a step period of the user; and means for using information about accelerations in said side to side direction to disambiguate whether the determined time period corresponds to the stride period of the user or to the step period of the user.

27. A method for determining movement information for a user that carries an accelerometer whilst moving, the method comprising:

receiving acceleration data from the accelerometer, the acceleration data defining accelerations experienced by the accelerometer resulting from movement of the user, the accelerations being defined relative to a frame of reference associated with the accelerometer;

applying to the acceleration data or to data derived from the acceleration data a transformation for transforming the frame of reference to a frame of reference of the user that includes a direction of travel of the user and a side to side direction transverse to the direction of travel of the user;

analysing the acceleration data or data derived from the acceleration data to determine a time period corresponding either to a stride period or to a step period of the user as the user is walking or running; and using information about accelerations in said side to side direction to disambiguate whether the determined time period corresponds to the stride period of the user or to the step period of the user.

28. A tangible computer readable medium comprising computer implementable instructions for causing a programmable computer device to become configured as an apparatus according to any of clauses 1 to 26.

29. A clinical trial system comprising a central computer that communicates with a plurality of user devices, each user device being arranged to collect acceleration data relating to movement of the user associated with the user device; and wherein the central computer or at least one user device comprises an apparatus according to any of clauses 1 to 26 for analysing acceleration data.

The invention claimed is:

1. An apparatus for determining movement information for a user that carries an accelerometer whilst moving, the apparatus comprising one or more processors and memory configured to:

receive acceleration data from the accelerometer, the acceleration data defining accelerations experienced by the accelerometer resulting from movement of the user, the accelerations being defined relative to a frame of reference associated with the accelerometer;

process the acceleration data or data derived from the acceleration data, including:

applying a transformation for transforming the frame of reference to a frame of reference of the user that includes a direction of travel of the user and a side to side direction transverse to the direction of travel of the user to provide transformed data or transformed data;

processing the transformed data to determine information about accelerations in said side to side direction;

determining a time period corresponding to a maximum peak in an autocorrelation function or a frequency function, wherein the determined time period is ambiguous and corresponds either to a stride period or to a step period of the user; and use said information about accelerations in said side to side direction to disambiguate whether the determined time period corresponds to the stride period of the user or to the step period of the user.

2. The apparatus according to claim 1, wherein the processor and memory are configured to use information about accelerations in said side to side direction and in said direction of travel to disambiguate whether the determined time period corresponds to the stride period of the user or to the step period of the user.

3. The apparatus according to claim 1, wherein the processor and memory are configured to determine a first autocorrelation function to determine said time period corresponding either to said stride period or to said step period of the user.

4. The apparatus of claim 3, wherein the processor and memory are configured to process the first autocorrelation function to identify a peak in the first autocorrelation function at an autocorrelation lag corresponding to the stride period of the user or to the step period of the user.

5. The apparatus of claim 4, wherein the processor and memory are configured to process the first autocorrelation function to identify the highest peak in the first autocorrelation function after a zero lag peak and to determine the time period corresponding to the stride period of the user or to the step period of the user as the autocorrelation lag associated with the identified highest peak.

6. The apparatus according to claim 4, wherein said processor and memory are configured to determine a second autocorrelation function of the accelerations in said side to side direction and are configured to disambiguate whether the time period corresponds to the stride period or the step period in dependence upon whether or not the second autocorrelation function includes a peak around the autocorrelation lag corresponding to the step or stride period.

7. The apparatus according to claim 4, wherein said processor and memory are configured to determine a second autocorrelation function of the accelerations in said side to side direction and a third autocorrelation function of the accelerations in said direction of travel and are configured to disambiguate whether the time period corresponds to the stride period or the step period in dependence upon whether or not the second autocorrelation function includes a peak around the autocorrelation lag corresponding to the step or stride period.

8. The apparatus according to claim 7, wherein the processor and memory are configured to use the first, second and third autocorrelation functions to confirm that the user is walking or running or not walking or not running.

9. The apparatus according to claim 3, wherein said first autocorrelation function is calculated on said accelerometer data or on data derived from said accelerometer data.

10. The apparatus of claim 1, wherein the processor and memory are configured to determine and apply a first transformation that aligns a first axis of the accelerometer data or data derived from the accelerometer data with a vertical axis.

11. The apparatus of claim 10, wherein the processor and memory are configured to determine and apply a second transformation that aligns a second axis of the accelerometer data or data derived from the accelerometer data with said direction of travel and a third axis of the accelerometer data or data derived from the accelerometer data with said side to side direction.

12. The apparatus according to claim 1, wherein the processor and memory are configured to:
process the transformed data to determine information about accelerations in said direction of travel;
determine that the determined time period corresponds to a stride period of the user when the information about accelerations in the side to side direction matches information about accelerations in the direction of travel; and
determine that the determined time period corresponds to a step period of the user when the information about accelerations in the side to side direction does not match the information about accelerations in the direction of travel.

13. The apparatus of claim 1, wherein the frame of reference of the user comprises a vertical direction transverse to both the direction of travel and the side to side direction.

14. The apparatus according to claim 1, wherein the processor and memory are configured to process the acceleration data to identify periods of walking or running within the acceleration data and is configured to determine said time period corresponding either to a stride period or to a step period of the user using acceleration data from within an identified period of walking or running.

15. The apparatus according to claim 1, wherein the processor and memory are configured to determine the direction of travel and the side to side direction as orthogonal directions in a horizontal plane that have the most and the least variability in the received acceleration data such that the direction with most variability in the acceleration data corresponds to the forwards/backwards direction and the direction with least variability in the acceleration data corresponds to the side to side direction.

16. The apparatus according to claim 1, wherein the processor and memory are further configured to use the disambiguated step period or stride period to determine a step count of the user for movements corresponding to walking or running.

17. The apparatus according to claim 1, wherein the apparatus forms part of a user device carried by the user and wherein the accelerometer forms part of the user device or is configured to communicate with the user device.

18. An apparatus according to claim 1 forming part of a clinical trial system comprising a central computer that communicates with a plurality of user devices, each user device being arranged to collect acceleration data relating to movement of the user associated with the user device; and wherein the central computer or at least one user device comprises the apparatus according to claim 1 for analyzing acceleration data.

19. The apparatus according to claim 1, wherein the one or more processors and memory are configured to apply the transformation to the acceleration data.

20. The apparatus according to claim 1, wherein the one or more processors and memory are configured to apply the transformation to data derived from the acceleration data.

21. The apparatus according to claim 20, wherein the data derived from the acceleration data comprises autocorrelation data obtained by determining an autocorrelation function of the acceleration data.

22. The apparatus according to claim 1, wherein the autocorrelation function or the frequency function is determined on the acceleration data.

23. The apparatus according to claim 1, wherein the autocorrelation function or the frequency function is determined on the transformed data.

24. An apparatus for determining movement information for a user that carries an accelerometer whilst moving, the apparatus comprising one or more processors and memory configured to:
receive acceleration data from the accelerometer, the acceleration data defining accelerations experienced by the accelerometer resulting from movement of the user, the accelerations being defined relative to a frame of reference associated with the accelerometer;
apply a transformation for transforming the frame of reference to a frame of reference of the user that includes a purported direction of travel of the user and a side to side direction transverse to the purported direction of travel of the user to provide transformed acceleration data or transformed data derived from the acceleration data that includes i) acceleration data for accelerations in said purported direction of travel, and ii) acceleration data for accelerations in said side to side direction;

determine a first autocorrelation function of the acceleration data or of the transformed acceleration data;

determine a second autocorrelation function of said acceleration data for accelerations in said purported direction of travel that is included in said transformed acceleration data;

determine a third autocorrelation function of said acceleration data for accelerations in said side to side direction that is included in said transformed acceleration; and determine if the user is walking or not walking or running or not running using the first, second and third autocorrelation functions.

25. A method for determining movement information for a user that carries an accelerometer whilst moving, the method comprising:

receiving acceleration data from the accelerometer, the acceleration data defining accelerations experienced by the accelerometer resulting from movement of the user, the accelerations being defined relative to a frame of reference associated with the accelerometer;

processing the acceleration data, including:

applying a transformation for transforming the frame of reference to a frame of reference of the user that includes a direction of travel of the user and a side to side direction transverse to the direction of travel of the user to provide transformed data;

processing the transformed data or the transformed data to determine information about accelerations in said side to side direction;

determining an autocorrelation function or a frequency function; and determining a time period corresponding to a maximum peak in the autocorrelation function or the frequency function, wherein the determined time period is ambiguous and corresponds either to a stride period or to a step period of the user as the user is walking or running; and using said information about accelerations in said side to side direction to disambiguate whether the determined time period corresponds to the stride period of the user or to the step period of the user.

26. The method according to claim 25, wherein the transformation is applied to the acceleration data.

27. The method according to claim 25, wherein the transformation is applied to data derived from the acceleration data.

28. The method according to claim 27, wherein the data derived from the acceleration data comprises autocorrelation data obtained by determining an autocorrelation function of the acceleration data.

29. The method according to claim 25, wherein the autocorrelation function or the frequency function is determined on the acceleration data.

30. The method according to claim 25, wherein the autocorrelation function or the frequency function is determined on the transformed data.

31. A method for determining movement information for a user that carries an accelerometer whilst moving, the method comprising:

receiving acceleration data from the accelerometer, the acceleration data defining accelerations experienced by the accelerometer resulting from movement of the user, the accelerations being defined relative to a frame of reference associated with the accelerometer;

applying a transformation for transforming the frame of reference to a frame of reference of the user that includes a purported direction of travel of the user and a side to side direction transverse to the purported direction of travel of the user to provide transformed acceleration data that includes i) acceleration data for accelerations in said purported direction of travel, and ii) acceleration data for accelerations in said side to side direction;

determining a first autocorrelation function of the acceleration data or of the transformed acceleration data;

determining a second autocorrelation function of said acceleration data for accelerations in said purported direction of travel that is included in said transformed acceleration data;

determining a third autocorrelation function of said acceleration data for accelerations in said side to side direction that is included in said transformed acceleration data; and determining if the user is walking or not walking or running or not running using the first, second and third autocorrelation functions.

* * * * *